US00PP36731P2

(12) United States Plant Patent
Yam

(10) Patent No.: US PP36,731 P2
(45) Date of Patent: Jun. 10, 2025

(54) ***FICUS* PLANT NAMED 'YAMKIMA'**

(50) Latin Name: *Ficus benjamina*
Varietal Denomination: YAMKIMA

(71) Applicant: Biostok Inc., Apopka, FL (US)

(72) Inventor: Tai Yam, Apopka, FL (US)

(73) Assignee: Biostok INC., Apopka, FL (US)

( * ) Notice: Subject to any disclaimer, the term of this patent is extended or adjusted under 35 U.S.C. 154(b) by 0 days.

(21) Appl. No.: 18/831,406

(22) Filed: Jan. 15, 2025

(51) Int. Cl.
*A01H 5/12* (2018.01)
*A01H 6/00* (2018.01)

(52) U.S. Cl.
USPC ..... Plt./211
CPC ..... *A01H 6/00* (2018.05)

(58) Field of Classification Search
USPC ..... Plt./211
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct variety of *Ficus* plant named 'YAMKIMA' which is characterized by a compact and densely foliaged growth habit, pale yellow-green juvenile foliage, generally appearing as a light cream yellow coloration, that is flecked and blotched with green and greyed-green, dark green mature foliage that is flecked and blotched with a combination of light yellow-green, white, and greyed-green, and the uniformity and stability of these characteristics from generation to generation.

3 Drawing Sheets

Latin name of the genus and species: The Latin name of the genus and species of the novel variety disclosed herein is *Ficus benjamina.*

Variety Denomination: The inventive variety of *Ficus* disclosed herein has been given the variety denomination 'YAMKIMA'.

BACKGROUND OF THE INVENTION

Parentage: 'YAMKIMA' originated as a naturally occurring, whole-plant mutation of *Ficus benjamina* 'Natasja' (not patented). The inventor discovered the mutation in May of 2018 at a commercial greenhouse in Apopka, Florida, growing amongst a cultivated population of 'Natasja' plants. The mutation was noted for its unique variegation relative to the parent and all other progeny and was subsequently isolated for further evaluation in order to confirm the distinctness and stability of the characteristics first observed. Upon confirmation of distinctness and stability, 'YAMKIMA' was selected for commercialization.

Asexual Reproduction: In June 2018, stem cuttings were first used to propagate 'YAMKIMA', at a commercial greenhouse in Apopka, Florida. Through eight subsequent generations of asexual reproduction, the unique features of this cultivar have proven to be stable and true to type.

SUMMARY OF THE INVENTION

The cultivar 'YAMKIMA' has not been observed under all possible environmental conditions. While the genotype of this variety may not change, the phenotype may be susceptible to changes with varying environmental factors such as temperature, day length, and light intensity. The following traits have been repeatedly observed and are determined to be the unique characteristics of 'YAMKIMA'. These characteristics in combination distinguish 'YAMKIMA' as a new and distinct *Ficus* cultivar:

1. *Ficus* 'YAMKIMA' exhibits a compact and densely-foliaged growth habit; and
2. *Ficus* 'YAMKIMA' exhibits small lanceolate leaves; and
3. *Ficus* 'YAMKIMA' exhibits pale yellow-green juvenile foliage, generally appearing as a light cream yellow coloration, that is flecked and blotched with green and greyed-green; and
4. *Ficus* 'YAMKIMA' exhibits dark green mature foliage that is flecked and blotched with a combination of light yellow-green, white, and greyed-green.

BOTANICAL DESCRIPTION OF THE PLANT

Figure 1:
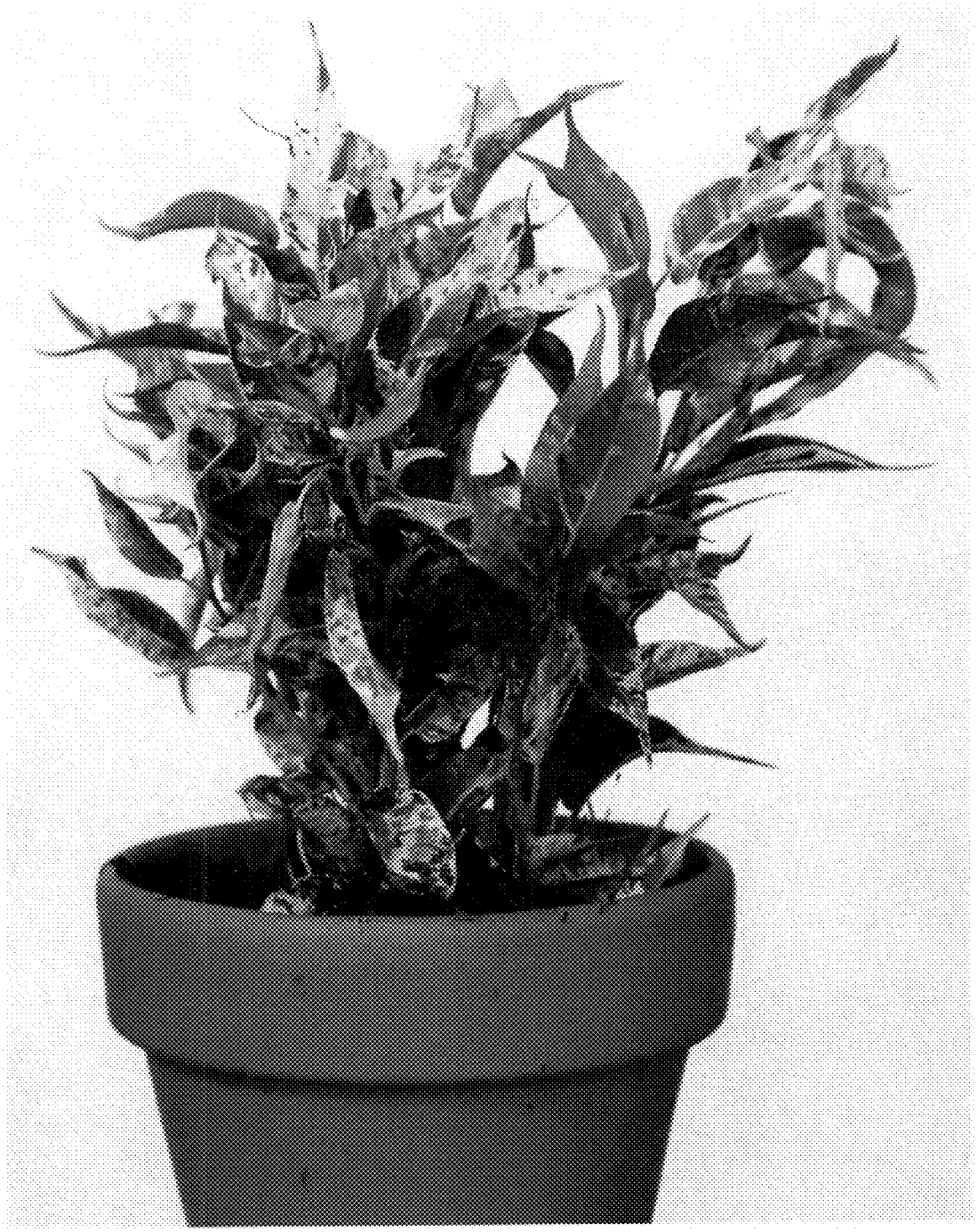
FIG. 1 illustrates, as nearly true as it is reasonably possible to make the same in color photographs of this type, an exemplary plant of 'YAMKIMA' grown in a commercial greenhouse in Apopka, Florida. This plant is approximately 12 months old, planted in a 9 cm stone pot.
Figure 2:
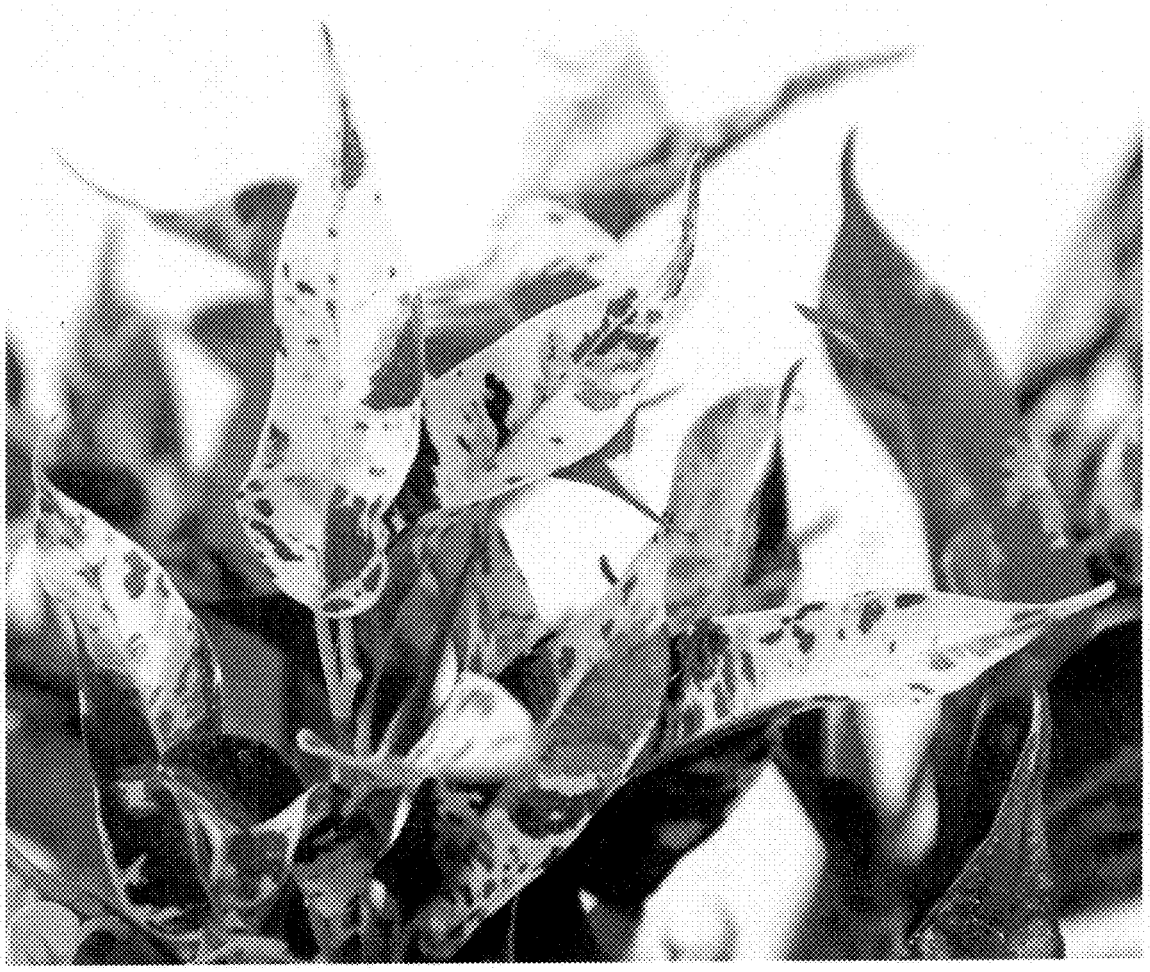
FIG. 2 illustrates, as nearly true as it is reasonably possible to make the same in color photographs of this type, the typical juvenile foliage of 'YAMKIMA'.
Figure 3:
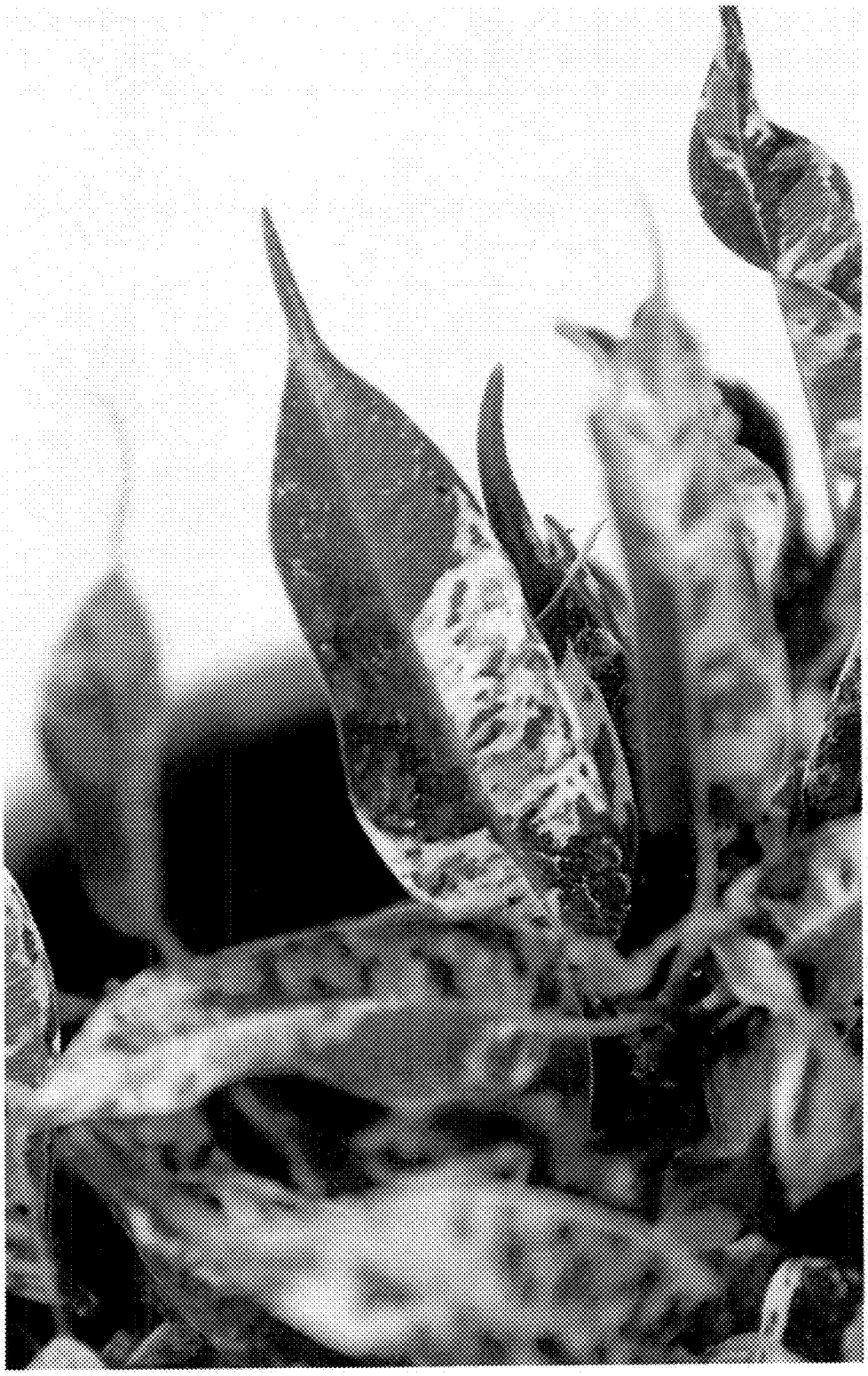
FIG. 3 illustrates, as nearly true as it is reasonably possible to make the same in color photographs of this type, the typical mature foliage of 'YAMKIMA'.

The following observations and measurements were made in April of 2021 and describe a 12-month-old 'YAMKIMA' plant grown in a 9 cm nursery pot at a greenhouse in Apopka, Florida. The plants were produced in a climate-controlled greenhouse, utilizing production protocols for

*Ficus* sp. which consisted of supplemental slow-release fertilizer applications and chemical pest control measures as needed, full sun exposure, and regular irrigation by way of ebb and flood benches. No supplemental lighting was used during production.

Those skilled in the art will appreciate that certain characteristics of 'YAMKIMA' will vary with the age of the plant. 'YAMKIMA' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'YAMKIMA' as well as comparisons with the parent plant and most similar commercial variety of *Ficus* are provided below.

Plant description:

*Growth habit*.—Broad, upright to spreading perennial.

*Plant form*.—Broad obovate.

*Average height*.—13.0 cm.

*Plant spread*.—15.9 cm.

*Propagation*.—Type — Stem cuttings. Time to produce a rooted cutting — Approximately 40 days to produce a rooted cutting at approximately 25 degrees Celsius. Time to produce a finished plant — Approximately 15 weeks to produce a marketable finished plant in a 14 cm pot.

*Disease resistance*.—'YAMKIMA' shows similar susceptibility and resistance of diseases to other *Ficus benjamina* varieties.

*Environmental tolerances*.—Adapt to, at least, USDA Zones 10 through 12 and temperatures as high as 40 degrees Celsius; moderate to high tolerance to rain; moderate tolerance to wind.

Root system:

*General*.—Moderately dense, moderately branched rooting; roots are slightly fibrous.

*Distribution in the soil profile*.—Moderately deep.

*Diameter of roots*.—1.0 mm, on average.

*Texture*.—Smooth and glabrous.

*Color*.—Greyed-yellow, nearest to a combination of RHS 160C and 160D.

Stem:

*General branching habit*.—Basally branching main stems, with no lateral branching.

*Main stems*.—Quantity — 15.Length — 9.3 cm. Diameter — 1.2 cm. Internode length — 0.85 cm. Attitude — Upright; at an average of 20 degrees from vertical. Aspect — Terete. Strength — Strong. Texture — Smooth when immature and developing striations and defoliated bark as the stems age. Luster — Slightly glossy. Color of developing stems — Yellow-green, nearest to a mixture of RHS 145C and 145D. Color of mature stems — Yellow-green, nearest to RHS 152A. Color at internodes — Yellow-green, nearest to RHS 152A. Color, oldest wood — Greyed-green, nearest to RHS 197A, with grey-brown striations and exfoliated bark that is colored nearest to a combination of RHS 199C and 199D.

Foliage:

*Arrangement*.—Alternate.

*Division*.—Simple.

*Quantity*.—11 leaves per stem.

*Attitude*.—At an average angle of 40 degrees to the branch.

*Shape*.—Lanceolate.

*Aspect*.—Moderately carinate with light longitudinal spiraling.

*Length*.—4.0 cm.

*Width*.—1.3 cm.

*Apex*.—Long, narrow apiculate to narrow aristate.

*Base*.—Obtuse.

*Margin*.—Entire, slightly to moderately repand.

*Texture and luster of the adaxial surface*.—Smooth, glabrous and moderately glossy.

*Texture and luster of the abaxial surface*.—Smooth, glabrous and slightly. glossy.

*Color*.—Juvenile foliage, adaxial surface — Yellow-green, nearest to a combination of RHS 150D, 154D, and a mixture of 150D and 154D; irregularly and densely blotched and flecked with a combination of green and greyed-green, nearest to RHS 141A, 143A, 143B, 191B, and 191D. Juvenile foliage, abaxial surface — Yellow-green, nearest to a combination of RHS 150D, 154D, and a mixture of 150D and 154D; irregularly and densely blotched and flecked with a combination of green and yellow-green, nearest to RHS 143B, 144A, 148C, and 148D. Mature foliage, adaxial surface — Green, nearest to a mixture of RHS NN137A and 139A, yet darker, and irregularly and densely blotched and flecked with a combination of yellow-green, white, and greyed-green; RHS 145D, 150D, 157A, 157B, 191A, and 191B. Mature foliage, abaxial surface — Green, nearest to RHS and 137C, and irregularly and densely blotched and flecked with a combination of green, yellow-green, and greyed-green; RHS 138A, 138B, 145C, 145D, 191B, and 191C.

*Venation*.—Pattern — Pinnate. Color, adaxial surface — Green, nearest RHS 138A. Color, abaxial surface — Yellow-green, nearest to a combination of RHS 145B and 145C.

Petiole:

*Length*.—0.75 cm.

*Diameter*.—0.1 cm.

*Strength*.—Strong.

*Texture*.—Smooth, glabrous.

*Luster*.—Slightly glossy.

*Color, adaxial surface*.—Green, nearest to RHS 138B.

*Color, abaxial surface*.—Green, nearest to a combination of RHS 138B and 138C.

Inflorescence: No flowering has been observed to date.

COMPARISON WITH THE PARENT PLANT

Plants of the new cultivar 'YAMKIMA' differ from the parent, *Ficus benjamina* 'Natasja' (not patented), in the following characteristics described in Table 1 below.

TABLE 1

| Characteristic | 'YAMKIMA' | 'Natasja' |
|---|---|---|
| General coloration of the juvenile foliage. | Pale yellow-green, generally appearing as a light cream-yellow coloration, and irregularly blotched and flecked with green and greyed-green. | Homogenously light green. |
| General coloration of the mature foliage. | Dark green, and irregularly blotched and flecked with a combination of light yellow-green, white, and greyed-green. | Not variegated; homogenously green. |

COMPARISON WITH THE CLOSEST KNOWN COMPARATOR

Plants of the new cultivar 'YAMKIMA' differ from the closest known commercial comparator, *Ficus* 'Samantha' (not patented), in the following characteristics described in Table 2 below.

TABLE 2

| Characteristic | 'YAMKIMA' | 'Samantha' |
|---|---|---|
| Growth habit. | More spreading than 'Samantha'. | More upright than 'YAMKIMA'. |
| Plant size. | Smaller than 'Samantha' and, thus, suitable for cultivation in smaller container sizes. | Larger than 'YAMKIMA' and not suited for cultivation in small container sizes. |
| Foliage size. | Smaller than 'Samantha'. | Larger than 'YAMKIMA', |
| General coloration of the mature foliage. | Dark green, and blotched and flecked with light yellow-green, white, and greyed-green. | Mid-green, and broadly and irregularly margined with a cream white. |

That which is claimed is:

1. A new and distinct variety of *Ficus* plant named 'YAMKIMA', substantially as described and illustrated herein.

* * * * *